US008388529B2

(12) United States Patent
Fueyo et al.

(10) Patent No.: US 8,388,529 B2
(45) Date of Patent: Mar. 5, 2013

(54) DIFFERENTIAL DIAGNOSIS OF NEUROPSYCHIATRIC CONDITIONS

(75) Inventors: Joanna Lynn Fueyo, Brighton, MA (US); Robert Lee Angell, Salt Lake City, UT (US); Robert R. Friedlander, Southbury, CT (US); James R. Kraemer, Santa Fe, NM (US)

(73) Assignee: International Business Machines Corporation, Armonk, NY (US)

( * ) Notice: Subject to any disclaimer, the term of this patent is extended or adjusted under 35 U.S.C. 154(b) by 728 days.

(21) Appl. No.: 12/169,339

(22) Filed: Jul. 8, 2008

(65) Prior Publication Data

US 2010/0010316 A1    Jan. 14, 2010

(51) Int. Cl.
*A61B 5/00* (2006.01)
*G06K 9/00* (2006.01)
(52) U.S. Cl. .................. 600/300; 382/128; 382/131
(58) Field of Classification Search .................. None
See application file for complete search history.

(56) References Cited

U.S. PATENT DOCUMENTS

| | | | |
|---|---|---|---|
| 5,873,823 A | 2/1999 | Eidelberg et al. | |
| 7,244,231 B2 * | 7/2007 | Dewing et al. ............... | 600/300 |
| 7,929,737 B2 * | 4/2011 | Sirohey et al. ............... | 382/128 |
| 2005/0020903 A1 | 1/2005 | Krishnan et al. | |
| 2005/0038678 A1 | 2/2005 | Qian et al. | |
| 2005/0091191 A1 * | 4/2005 | Miller et al. ..................... | 707/1 |
| 2005/0215889 A1 | 9/2005 | Paterson, II | |
| 2006/0120584 A1 | 6/2006 | Hillman | |
| 2007/0129627 A1 * | 6/2007 | Profio et al. .................. | 600/407 |

FOREIGN PATENT DOCUMENTS

| | | |
|---|---|---|
| JP | 2005-237441 | 9/2005 |
| JP | 2006-204641 | 8/2006 |
| WO | WO 2007-019504 | 2/2007 |
| WO | WO2007019504 A | 2/2007 |
| WO | WO 2007/063656 A1 | 6/2007 |

OTHER PUBLICATIONS

U.S. Appl. No. 12/141,316, filed Jul. 8, 2008, Fueyo et al.
U.S. Appl. No. 12/169,402, filed Jul. 8, 2008, Fueyo et al.
U.S. Appl. No. 12/141,322, filed Jun. 18, 2008, Fueyo et al.
U.S. Appl. No. 12/169,329, filed Jul. 8, 2008, Fueyo et al.
U.S. Appl. No. 12/169,350, filed Jul. 8, 2008, Fueyo et al.
JP Office Action dated Aug. 4, 2009.

(Continued)

*Primary Examiner* — Henry M Johnson, III
*Assistant Examiner* — Shirley Jian
(74) *Attorney, Agent, or Firm* — Shimokaji & Assoc., PC

(57) ABSTRACT

A computer implemented method, apparatus, and computer program product for generating neuropsychiatric diagnoses. Quantitative information describing diagnostic characteristics associated with a patient is generated based on an analysis of a set of patient scans. The quantitative information comprises a set of indictors associated with regions of interest in the set of scans for the patient. The set of indicators of potential neuropsychiatric conditions is compared with a set of diagnostic signatures. A diagnostic signature comprises a set of indicators of a known neuropsychiatric condition. Matching signatures are identified. A matching signature is a diagnostic signature that corresponds to at least one indicator in the set of indicators to form a set of signatures. A diagnosis associated with each signature in the set of signatures is identified to form a set of potential diagnoses. The set of potential diagnoses is presented with links to relevant portion of the medical literature.

25 Claims, 8 Drawing Sheets

OTHER PUBLICATIONS

Aberle, Denise R. et al, Database Design and Implementation for Quantitative Image Analysis Research, IEEE Transactions on Information Technology in Biomedicine, vol. 9, No. 1, Mar. 2005, pp. 99-108.

Rahman, Mahmudur et al, "Medical Image Retrieval and Registration: Towards Computer Assisted Diagnostic Approach", Medical Information Systems: The Digital Hospital (IDEAS-DH'04), IEEE, Sep. 2004, pp. 78-89.

European Search Report dated Mar. 27, 2009.

Rahman, Mahmudur et al "Medical Image Retrieval and Registration: Towards Computer Assisted Diagnostic Approach", Medical Information Systems: The Digital Hospital (IDEAS-DH'04), IEEE, Sep. 2004, pp. 78-89.

* cited by examiner

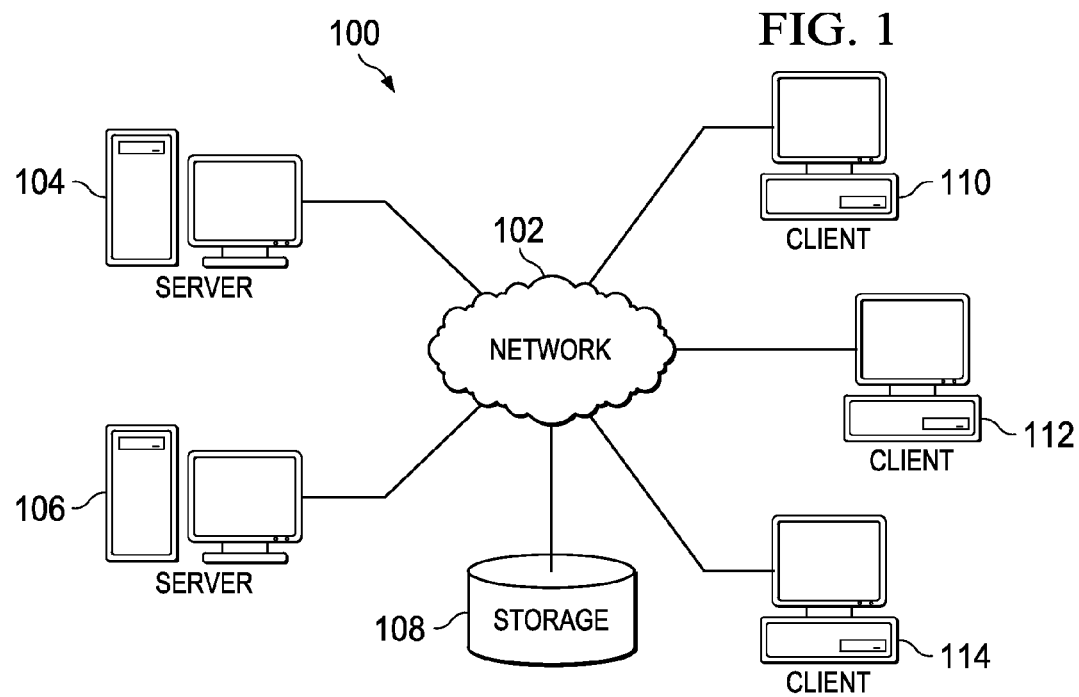
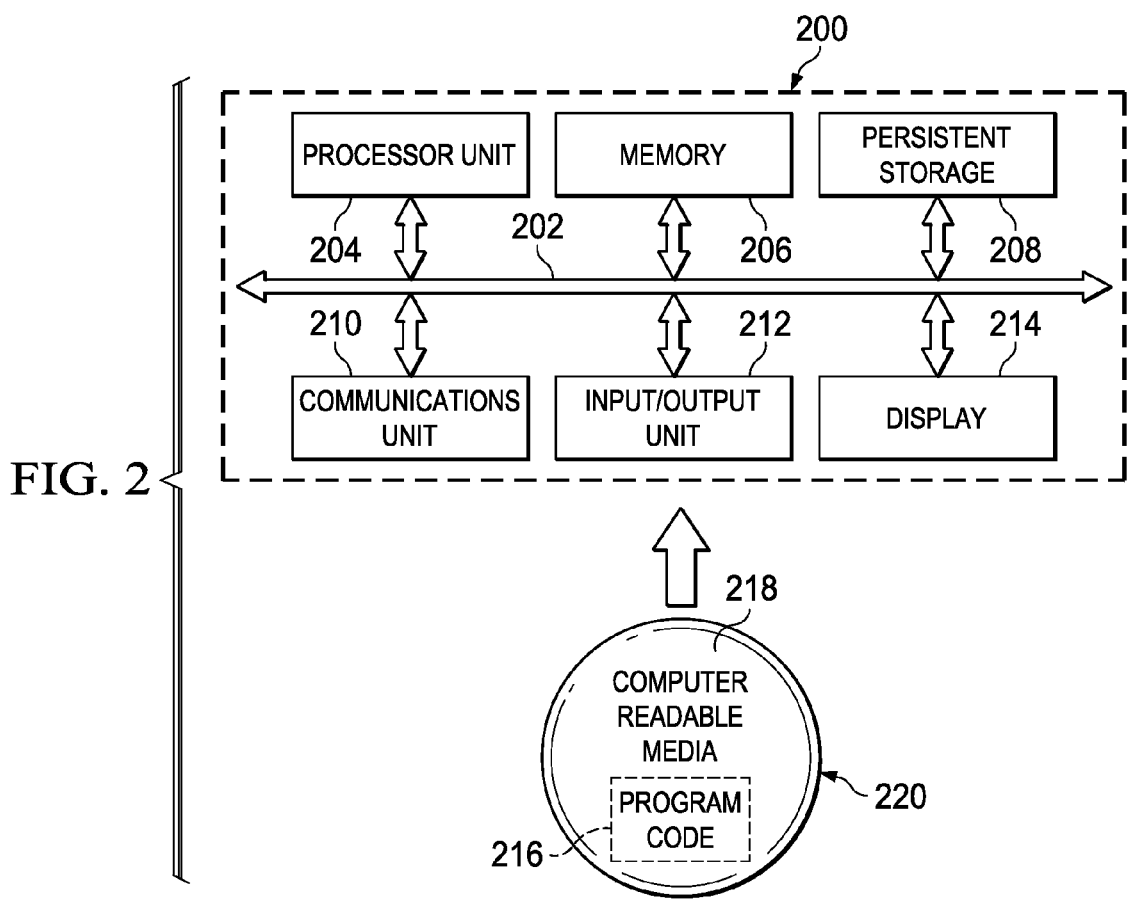

DIFFERENTIAL DIAGNOSIS OF NEUROPSYCHIATRIC CONDITIONS

BACKGROUND OF THE INVENTION

1. Field of the Invention

The present invention is related generally to a data processing system and in particular to a method and apparatus for improving neuropsychiatric diagnosis. More particularly, the present invention is directed to a computer implemented method, apparatus, and computer usable program code for improving differential diagnosis of neuropsychiatric disease via provision of quantitative information derived from correlation of neuroimage data and medical literature.

2. Description of the Related Art

Neuropsychiatric conditions have neurological features associated with the nervous system, as well as psychiatric features. Neuropsychiatric conditions may be treated using a variety of therapies, such as talk therapy, behavioral therapy, chemical therapy, and/or mechanical therapy. Chemical therapy refers to pharmacotherapy, such as, the utilization of drugs. Mechanical therapy includes electroconvulsive therapies (ECT). These therapies may be used separately or may be used in combination to treat patients diagnosed with neuropsychiatric disorders.

However, many of these patients may not receive the most effective treatments due to difficulties in accurately diagnosing patients with neuropsychiatric conditions. Patients that are accurately diagnosed may also suffer from the side effects of both effective therapies and trails of ineffective therapies. Furthermore, some patients may suffer for years as a result of poorly understood disease phenotype, particularly in cases involving the presentation of complex cases. In addition, when a condition is developing in a patient and the patient has not had a sufficient number of "episodes" for diagnosis or has only manifested a few early stage symptoms, it may be difficult or impossible to clearly and rapidly delineate a differential diagnosis.

BRIEF SUMMARY OF THE INVENTION

According to one embodiment of the present invention, a computer implemented method, apparatus, and computer program product for generating neuropsychiatric diagnoses is provided. The diagnostic engine generates quantitative information describing diagnostic characteristics associated with a patient based on an analysis of a set of patient scans. The quantitative information comprises a set of indicators of potential neuropsychiatric conditions associated with regions of interest in the set of scans for the patient. The diagnostic engine compares the set of indicators of potential neuropsychiatric conditions with a set of diagnostic signatures. A diagnostic signature comprises a set of indicators of a known neuropsychiatric condition. The diagnostic engine identifies matching signatures, wherein a matching signature is a diagnostic signature that corresponds to at least one indicator in the set of indicators to form a set of signatures. The diagnostic engine identifies a diagnosis associated with each signature in the set of signatures to form a set of potential diagnoses.

In one embodiment, the diagnostic engine identifies a weighting associated with each matching signature. A matching signature having a greater weighting is identified as a diagnosis having a higher degree of certainty than a diagnosis associated with a matching signature having a lower weighting.

In another embodiment, the diagnostic engine generates the quantitative information by deriving the quantitative information from a correlation of the regions of interest with the portions of interest in the medical literature. The diagnostic engine may also optionally generate the quantitative information by analyzing a medical history for the patient, clinical data, behavioral data, and/or cognitive data with the regions of interest and the portions of interest in the medical literature to form the quantitative information. The medical history comprises information describing previously diagnosed medical conditions of the patient, previously prescribed medications, and currently prescribed medications. The clinical data comprises results of laboratory tests, wherein laboratory tests comprises urinalysis, blood tests, thyroid tests, biopsies, cultures, electrolyte tests, genetic tests, hormone tests, and any other clinical or laboratory test results.

In one embodiment, a digital video analysis receives digital video data from a set of cameras. The digital video data comprises images of the patient. The digital video analysis generates the behavioral data by analyzing the video data. The behavioral data comprises metadata describing actions taken by the patient and events associated with the patient.

In another embodiment, the set of potential diagnoses includes an identification of each indicator in the set of potential neuropsychiatric indicators associated with each diagnosis in the set of diagnoses. The set of potential diagnoses may also include a link to a portion of the medical literature associated with each diagnosis in the set of diagnoses. In yet another embodiment, the diagnostic engine identifies the matching signatures by processing the set of indicators of potential neuropsychiatric conditions in a diagnostic model. The diagnostic model analyzes combinations of indicators in the set of indicators of potential neuropsychiatric conditions and compares the combinations of indicators with each signature in the set of diagnostic signatures to identify the matching signatures.

BRIEF DESCRIPTION OF THE SEVERAL VIEWS OF THE DRAWINGS

FIG. 1 is a pictorial representation of a network of data processing systems in which illustrative embodiments may be implemented;

FIG. 2 is a block diagram of a data processing system in which illustrative embodiments may be implemented;

DETAILED DESCRIPTION OF THE INVENTION

Figure 3A:
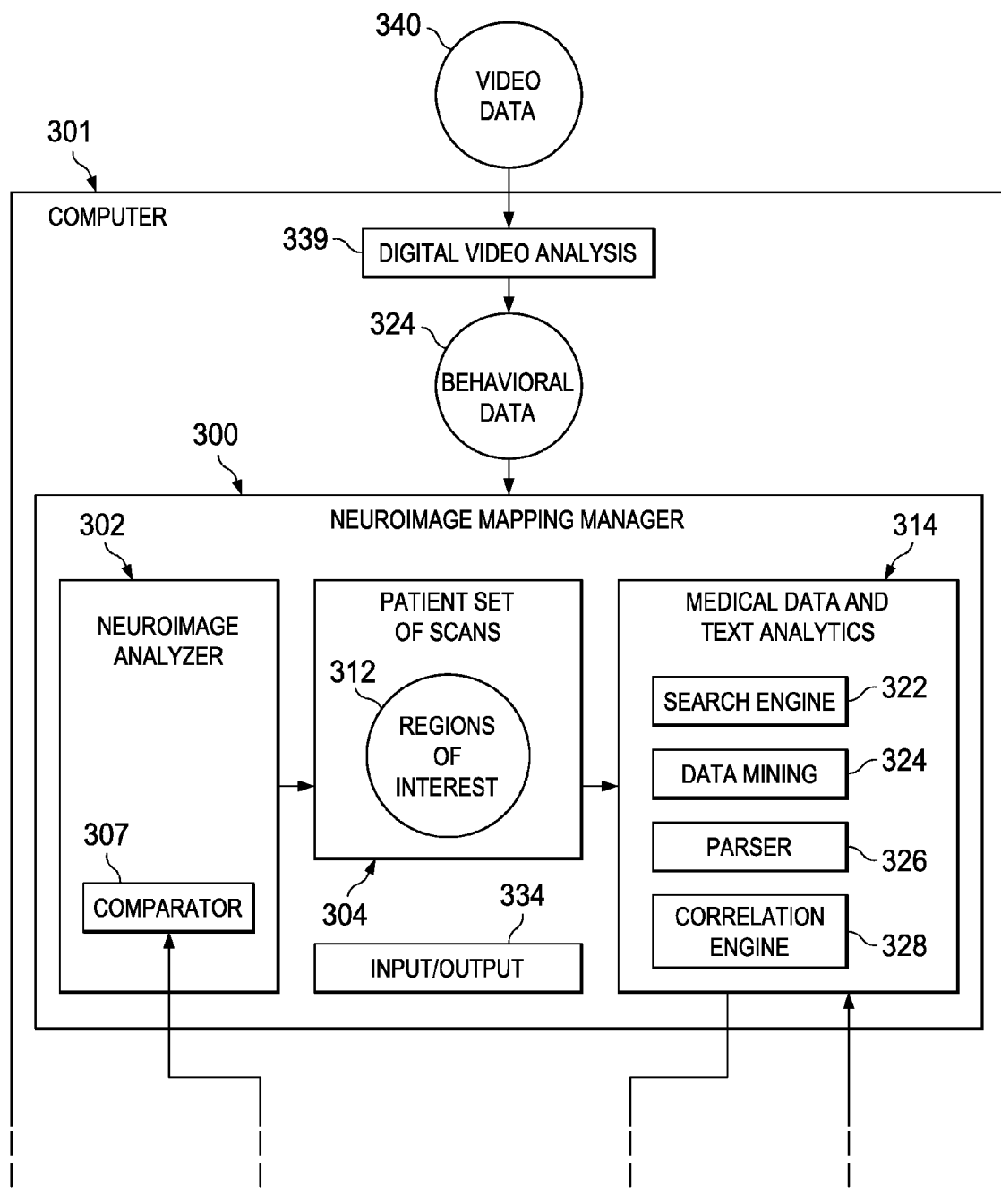
FIGS. 3A and 3B is a block diagram of a neuroimage mapping manager in accordance with an illustrative embodiment.

As will be appreciated by one skilled in the art, the present invention may be embodied as a system, method or computer program product. Accordingly, the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present invention may take the form of a computer program product embodied in any tangible medium of expression having computer usable program code embodied in the medium.

Any combination of one or more computer usable or computer readable medium(s) may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CDROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, etc.

Computer program code for carrying out operations of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions.

These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

FIG. 1 depicts a pictorial representation of a network of data processing systems in which illustrative embodiments may be implemented. Network data processing system 100 is a network of computers in which the illustrative embodiments may be implemented. Network data processing system 100 contains network 102, which is the medium used to provide communication links between various devices and computers connected together within network data processing system 100. Network 102 may include connections, such as wire, wireless communication links, or fiber optic cables.

In the depicted example, server 104 and server 106 connect to network 102 along with storage unit 108. In addition, clients 110, 112, and 114 connect to network 102. Clients 110, 112, and 114 may be, for example, personal computers or network computers. In the depicted example, server 104 provides data, such as boot files, operating system images, and applications to clients 110, 112, and 114. Clients 110, 112, and 114 are clients to server 104 in this example. Network data processing system 100 may include additional servers, clients, and other devices not shown.

In the depicted example, network data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, network data processing system 100 also may be implemented as a number of different types of networks, such as for example, an intranet, a local area network (LAN), or a wide area network (WAN). FIG. 1 is intended as an example, and not as an architectural limitation for the different illustrative embodiments.

With reference now to FIG. 2, a block diagram of a data processing system is shown in which illustrative embodiments may be implemented. Data processing system 200 is an example of a computer, such as server 104 or client 110 in FIG. 1, in which computer usable program code or instructions implementing the processes may be located for the illustrative embodiments. In this illustrative example, data processing system 200 includes communications fabric 202, which provides communications between processor unit 204, memory 206, persistent storage 208, communications unit 210, input/output (I/O) unit 212, and display 214.

Processor unit 204 serves to execute instructions for software that may be loaded into memory 206. Processor unit 204 may be a set of one or more processors or may be a multi-processor core, depending on the particular implementation. Further, processor unit 204 may be implemented using one or more heterogeneous processor systems in which a main processor is present with secondary processors on a single chip. As another illustrative example, processor unit 204 may be a symmetric multi-processor system containing multiple processors of the same type.

Memory 206 and persistent storage 208 are examples of storage devices. A storage device is any piece of hardware that is capable of storing information either on a temporary basis and/or a permanent basis. Memory 206, in these examples, may be, for example, a random access memory or any other suitable volatile or non-volatile storage device. Persistent storage 208 may take various forms depending on the particular implementation. For example, persistent storage 208 may contain one or more components or devices. For example, persistent storage 208 may be a hard drive, a flash memory, a rewritable optical disk, a rewritable magnetic tape, or some combination of the above. The media used by persistent storage 208 also may be removable. For example, a removable hard drive may be used for persistent storage 208.

Communications unit 210, in these examples, provides for communications with other data processing systems or devices. In these examples, communications unit 210 is a network interface card. Communications unit 210 may provide communications through the use of either or both physical and wireless communication links.

Input/output unit 212 allows for input and output of data with other devices that may be connected to data processing system 200. For example, input/output unit 212 may provide a connection for user input through a keyboard and mouse. Further, input/output unit 212 may send output to a printer. Display 214 provides a mechanism to display information to a user.

Instructions for the operating system and applications or programs are located on persistent storage 208. These instructions may be loaded into memory 206 for execution by processor unit 204. The processes of the different embodiments may be performed by processor unit 204 using computer implemented instructions, which may be located in a memory, such as memory 206. These instructions are referred to as program code, computer usable program code, or computer readable program code that may be read and executed by a processor in processor unit 204. The program code in the different embodiments may be embodied on different physical or tangible computer readable media, such as memory 206 or persistent storage 208.

Program code 216 is located in a functional form on computer readable media 218 that is selectively removable and may be loaded onto or transferred to data processing system 200 for execution by processor unit 204. Program code 216 and computer readable media 218 form computer program product 220 in these examples. In one example, computer readable media 218 may be in a tangible form, such as, for example, an optical or magnetic disc that is inserted or placed into a drive or other device that is part of persistent storage 208 for transfer onto a storage device, such as a hard drive that is part of persistent storage 208. In a tangible form, computer readable media 218 also may take the form of a persistent storage, such as a hard drive, a thumb drive, or a flash memory that is connected to data processing system 200. The tangible form of computer readable media 218 is also referred to as computer recordable storage media. In some instances, computer recordable media 218 may not be removable.

Alternatively, program code 216 may be transferred to data processing system 200 from computer readable media 218 through a communications link to communications unit 210 and/or through a connection to input/output unit 212. The communications link and/or the connection may be physical or wireless in the illustrative examples. The computer readable media also may take the form of non-tangible media, such as communication links or wireless transmissions containing the program code.

The different components illustrated for data processing system 200 are not meant to provide architectural limitations to the manner in which different embodiments may be implemented. The different illustrative embodiments may be implemented in a data processing system including components in addition to or in place of those illustrated for data processing system 200. Other components shown in FIG. 2 can be varied from the illustrative examples shown.

As one example, a storage device in data processing system 200 is any hardware apparatus that may store data. Memory 206, persistent storage 208, and computer readable media 218 are examples of storage devices in a tangible form.

In another example, a bus system may be used to implement communications fabric 202 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 206 or a cache such as found in an interface and memory controller hub that may be present in communications fabric 202.

According to one embodiment of the present invention, a computer implemented method, apparatus, and computer program product for generating neuropsychiatric diagnoses is provided. Quantitative information describing diagnostic characteristics associated with a patient is generated based on an analysis of a set of patient scans. As used herein, the term "set" refers to one or more, unless otherwise specified. Diagnostic characteristics of interest comprise a set of indicators of potential neuropsychiatric conditions. The quantitative information comprises information associated with regions of interest in the set of scans for the patient.

The set of indicators of potential neuropsychiatric conditions is compared with a set of diagnostic signatures. A diagnostic signature comprises a set of indicators of a known neuropsychiatric condition. Matching signatures are identified. A matching signature is a diagnostic signature that corresponds to at least one indicator in the set of indicators to form a set of signatures. As used herein, the term "at least one" refers to a one, as well as two or more in any combination. Therefore, "at least one indicator" refers to one or more indicators. The at least one indicator may be, for example and without limitation, a single indicator, two indicators, or any other number of different indicators. A diagnosis associated with each signature in the set of signatures is identified to form a set of potential diagnoses. The set of potential diagnoses is presented. The set of potential diagnosis comprises a link to a portion of the medical literature associated with each diagnosis.

Figure 3B:
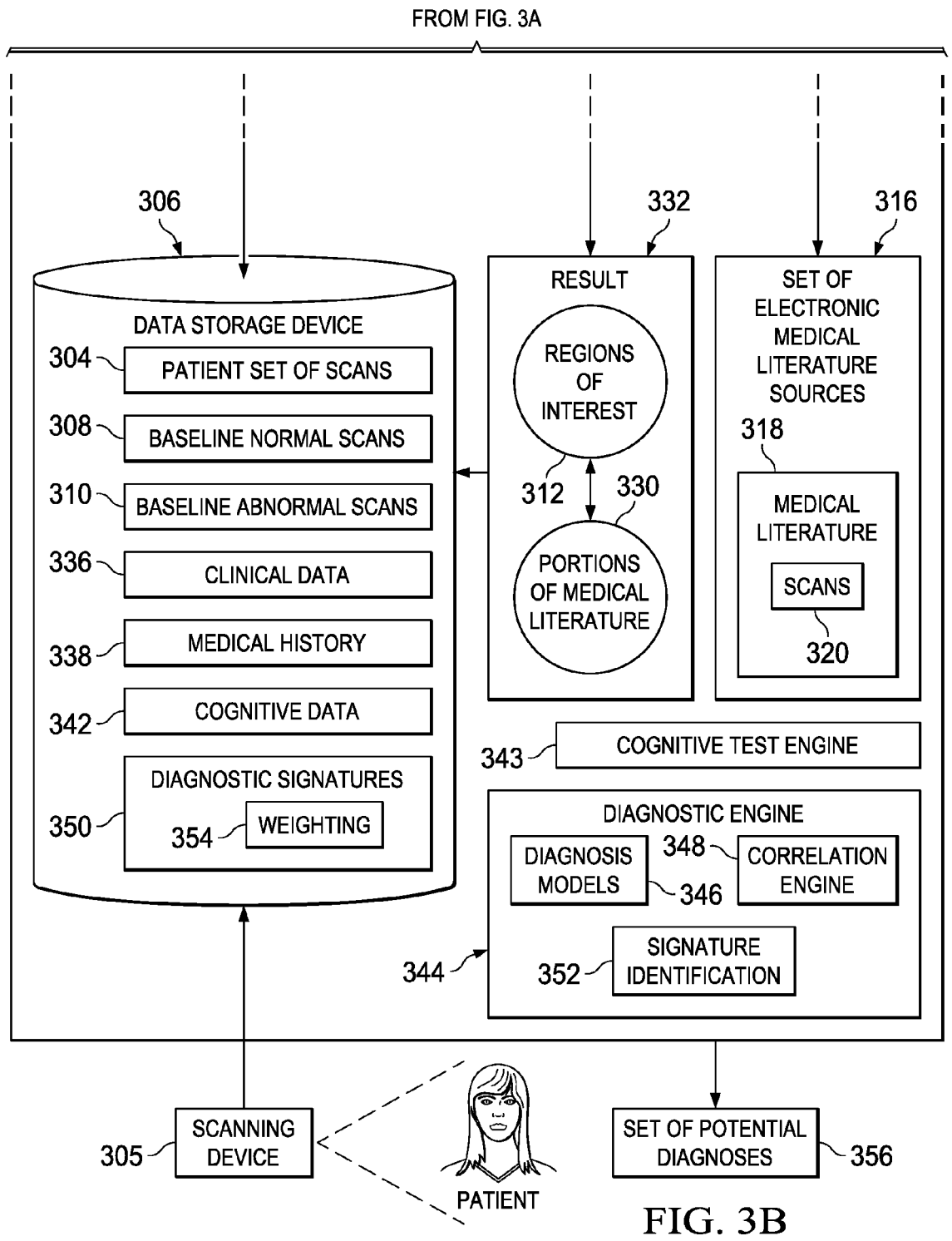

FIGS. 3A and 3B is a block diagram of a neuroimage mapping manager in accordance with an illustrative embodiment. Neuroimage mapping manager 300 is software for analyzing patient brain scans to identify regions of interest in the brain scans and generate links to portions of interest in the medical literature. Computer 301 may be implemented in any type of computing device, such as, without limitation, a server, a client, a laptop computer, a personal digital assistant (PDA), a smart phone, or any other known or available computing device shown in FIG. 1 and FIG. 2.

Neuroimage analyzer 302 receives patient set of scans 304. Patient set of scans 304 is a set of one or more scans of a patient's brain. Patient set of scans 304 may include functional magnetic resonance imaging (fMRI) scans, structural magnetic resonance imaging (sMRI) scans, positron emission tomography (PET) scans, and/or any other type of brain scans. In other words, patient set of scans 304 may include only positron emission tomography scans, only magnetic resonance imaging scans, or a combination of positron emission tomography scans and magnetic resonance imaging scans. The scans in patient set of scans 304 may be generated by one or more scanning devices, such as scanning device 305.

Scanning device 305 may be implemented as one or more of a functional magnetic resonance imaging device, a structural magnetic resonance imaging device, a positron emission tomography device, or any other type of device for generating scans of a human patient's brain. As used herein, the term "patient" is not limited to a patient admitted in a hospital. The term "patient" may refer to any person obtaining medical care, consulting a medical practitioner, participating in a medical study, obtaining medical advice, or otherwise participating in medical tests and/or medical procedures.

Scanning device 305 in this example is a single scanning device. However, scanning device 305 may also include two or more scanning devices. Scanning device 305 optionally saves the scans of the patient's brain in data storage device 306. Data storage device 306 may be implemented as a hard drive, a flash memory, a main memory, read only memory (ROM), a random access memory (RAM), or any other type of data storage device. Data storage may be implemented in a single data storage device or a plurality of data storage devices. Thus, neuroimage analyzer 302 may receive the scans in patient set of scans 304 from scanning device 305 as each scan is generated, or neuroimage analyzer 302 may retrieve the scans from a pre-generated set of scans stored in data storage device 306.

Comparator 307 is a software component that compares patient set of scans 304 to baseline normal scans 308 and/or baseline abnormal scans 310 to identify regions of interest 312. A region of interest is an area in a scan that shows an indication of a potential abnormality, a potential illness, a potential disease, a potential condition, or any other deviation from what would be expected in a scan of the region for a healthy individual having similar characteristics as the patient. The similar characteristics may include, without limitation, an age range of the patient, gender, pre-existing conditions, or other factors influencing the development, function, structure, and appearance of an area of the brain as shown in a scan.

Baseline normal scans 308 may include, without limitation, a set of one or more brain scans for average, healthy subjects having one or more characteristics in common with the patient. The characteristics in common may be age, gender, pre-existing conditions, profession, place of residence, nationality, or any other characteristic. For example, if the patient is a sixteen year old female, baseline normal scans 308 may include scans of normal, healthy female subjects between the ages of fourteen and eighteen. Comparator 307 compares one or more areas in each scan in patient set of scans 304 with corresponding areas in one or more scans in baseline normal scans 308 to identify areas of the patient's scans that are consistent with the scans of normal, healthy subjects and to identify areas of the scans that are inconsistent with the scans of normal, healthy subjects. An area in a scan that is inconsistent with the corresponding areas in baseline normal scans 308 are identified as a region of interest in regions of interest 312. A region identified in regions of interest 312 may indicate a potential abnormality, illness, or condition. However, each region in regions of interest 312 are not required to definitively indicate an abnormality, illness, condition, or other deviation from the norm.

Baseline abnormal scans 310 is a set of one or more scans of subjects having one or more characteristics in common with the patient and diagnosed with an identified condition. The identified condition may be a disease, an illness, a deformity, an abnormality, or any other identified deviation from the norm. For example, if the patient is a male, age thirty five, and diagnosed with diabetes, the baseline abnormal scans may include scans of male patients between the ages of thirty and forty and having a variety of known neuropsychiatric disorders. Comparator 307 compares regions in each scan in patient set of scans 304 with one or more scans in baseline abnormal scans 310 to identify regions of interest in the patient's scans that show indications of disorders, illness, disease, or abnormalities. A region in a scan may show indications of a potential illness, condition, abnormality, or neuropsychiatric disorder if the region in the patient's scan is consistent with a corresponding region in a brain scan of a subject having a known illness, condition, abnormality, or neuropsychiatric disorder. Thus, neuroimage analyzer 302 analyzes patient set of scans 304 to identify regions of interest in the scans based on baseline normal scans and/or baseline disorder scans for identified illnesses, abnormalities, diseases, disorders, or other known conditions.

Medical data and text analytics 314 is a software component for searching set of electronic medical literature sources 316 for medical literature relevant to regions of interest 312 in patient set of scans 304. Set of electronic medical literature sources 316 is a set of one or more sources of medical literature 318. Set of electronic medical literature sources 316 may include both online medical literature sources that are accessed by medical data and text analytics 314 via a network connection, as well as off-line medical literature sources that may be accessed without a network connection. An example of an electronic medical literature source includes, without limitation, PUBMED. Medical literature 318 is any literature, journal article, medical study results, medical text, pharmaceutical studies, or any other medical information in an electronic format. Medical literature 318 may include scans 320, such as magnetic resonance imaging scans, positron emission tomography scans, or any other type of brain scans.

Medical data and text analytics 314 comprises search engine 322. Search engine 322 is any type of known or available information retrieval software for locating medical literature that is relevant to regions of interest 312 in set of electronic medical literature sources 316. Search engine 322 may be software for searching data storage devices on a computer system or a web search tool for searching for medical information on the World Wide Web. Search engine 322 may also make queries into databases, information systems, and other medical literature information sources to locate information relevant to regions of interest 312.

Data mining 324 is a software tool for searching through information available from one or more sources and retrieving medical information relevant to regions of interest 312. Data mining 324, search engine 322, or any other software for locating relevant information may be used to search set of electronic medical literature sources 320 for relevant medical literature. Searching through the information from one or more sources may include, without limitation, using at least one of data mining, search engines, pattern recognition, queries to identify the relevant medical literature in the medical literature available from the set of electronic medical literature sources, data mining cohort, pattern recognition cohort, search engine cohort, any other cohort appliance of interest, or any combination of these. For example, and without limitation, the searching may include only search engine, include data mining and search engines, or include data mining pattern recognition, and queries.

A cohort is a group of one or more objects having a common characteristic. For example, a data mining cohort may be, without limitation, a group of one or more objects associated with performing data mining techniques to identify desired data from a data source. A pattern recognition cohort may be, without limitation, a group of pattern recognition software applications that identify patterns in data, such as medical data.

Parser 326 is software for parsing medical literature 318 text into a form suitable for further analysis and processing. Parser 326 may be implemented as any type of known or available parser. Correlation engine 328 correlates portions of medical literature 318 with regions of interest 312 to form portions of medical literature 330 that are relevant or associated with regions of interest 312. A portion of medical literature is a section of medical literature text and/or one or more scans that describes a region of interest, describes a condition, illness, deformity, abnormality, disease, or other cause for an appearance of a region of interest, an area in a scan that is the same or similar to an area of interest, an area in a scan in scans 320 or a portion of text in a medical literature document that is otherwise associated with a characteristic, feature, structure, indicator of brain chemistry, indicator of brain function, or other feature shown in an area of interest in a patient's brain scan.

For example, if a region of interest in patient's brain scan indicates an enlargement of a brain ventricle, a scan in scans 320 in medical literature 318 showing a similar enlargement of the brain ventricle is a portion of medical literature that is relevant or associated with regions of interest 312. Likewise, if a section of a medical journal article in an electronic format in medical literature 318 describes various causes of enlargement of a brain ventricle, that section of the medical literature is also relevant or associated with regions of interest 312. Thus, in this example, portions of medical literature 330 include both the scan showing the enlargement of the ventricle in a different patient and the portion of the medical journal article discussing possible causes of an enlargement of the ventricles in patients.

In this manner, medical data and text analytics 314 is capable of automatically searching for electronic medical literature, identifying portions of the medical literature that are relevant to a particular patient's diagnosis and/or treatment, and correlating each item, such as a scan or a section in a journal article, to each region of interest in the patient's brain scans. When a user wishes to view all the relevant medical literature associated with a particular region of interest, the user can simply request all the portions of medical literature correlated to the particular region of interest. In response, neuroimage mapping manager 300 only provides the portions of medical literature 318 from a plurality of medical literature sources that may be useful to the user, rather than providing the full text of all medical journal articles that have certain key words or search phrases, as is currently done.

Neuroimage mapping manager 300 may also generate result 332, including regions of interest 312 and a set of links to portions of medical literature 330. Result 332 may optionally include an identification of a source and/or citation for the source of each portion of medical literature. The set of links to portions of medical literature 330 may also optionally be embedded in patient set of scans 304 and/or embedded within regions of interest 312 in patient set of scans. The set of links to portions of medical literature 344 may also optionally be presented as a separate result apart from patient set of scans 304 and/or apart from regions of interest 312. In another embodiment, the set of links to portions of medical literature 330 are embedded in an electronic medical file for the patient or a file for brain scan results for one or more patients. A user selects a link in the set of links to view a portion of medical literature associated with a region of interest. In such a case, the portions of medical literature 330 in the patient's medical file may include a set of links to patient set of scans 304 and/or a set of links to regions of interest 312. In such a case, each portion of the medical literature, such as a scan or a section of a medical journal article, may include a link to the region of interest that is associated with or relevant to that portion of the medical literature. Likewise, all the portions of the medical literature that are relevant to a particular region of interest may include a single link to that particular region of interest rather than each portion of the medical literature including a separate link to the particular region of interest or regions of interest associated with the portions of the medical literature.

The portion of medical literature may be a scan only, text only, or a combination of text and one or more scans. The portion of medical literature may be an entire or complete item, such as a complete medical journal article or a complete section of a medical textbook, if the entire journal article or complete section of the medical text is relevant to the features shown in a particular region of interest. The portion of medical literature may also be a portion of a journal article, a portion of a section of a medical textbook, or other part of an item of medical literature. In such a case, a user may optionally select to view the entire journal article or the entire medical text rather than viewing only the relevant portion of the journal article or medical text.

In this embodiment, baseline normal scans 308 and baseline abnormal scans 310 are pre-generated and available for retrieval from data storage device 306. However, in another embodiment, medical data and text analytics 314 searches set of electronic medical literature sources 316 for scans of normal, healthy subjects to create baseline normal scans 308. Medical data and text analytics 316 also searches set of medical literature sources 320 for scans of subjects having known abnormalities, deformities, illnesses, ailments, diseases, or other neuropsychiatric disorders to create baseline abnormal scans 310.

Thus, neuroimage mapping manager 300 provides data and text analytics to automatically determine regions of a patient's brain affected by neuropsychiatric conditions and/or other illness or abnormality as depicted in functional neuroimage data. Neuroimage data is data associated with a brain scan, such as functional magnetic resonance imaging and positron emission tomography scans. Neuroimage mapping manager 300 applies technologies to data, such as heuristics, which automatically correlate the features identified in regions of interest 312 with relevant portions of medical literature 320 in medical literature 318 that describes regions of interest 312.

Input/output 334 may be implemented as any type of input and/or output device for presenting output to a user and receiving input from a user. For example, input/output 334 may present regions of interest 312 to a user and/or receive a selection of one or more regions of interest from a user. Input/output 334 may also be used to present result 332, potential diagnoses, or other information to a user. Neuroimage analyzer 302 may optionally present the automatically selected regions of interest to the user using input/output 334. The automatically selected regions of interest may be presented using a display device to present the regions of interest in a visual format, using an audio device to present the regions of interest to the user in an audio format, using a tactile interface that may be read by the visually impaired, using a combination of audio and visual devices, using a combination of audio and tactile devices, or any other presentation device.

The user may utilize input/output 334 to choose to select one or more additional regions of interest in patient set of scans 304. In such a case, neuroimage analyzer 302 adds the manually selected set of one or more regions of interest to regions of interest 312. In one embodiment, the regions of interest that are not automatically selected by neuroimage analyzer 302 and/or regions of interest that are not manually selected by the user are automatically removed by neuroimage analyzer 302. In another embodiment, the user may choose to manually de-select or remove one or more regions of interest that was automatically selected by neuroimage analyzer 302. In such a case, neuroimage analyzer 302 automatically removes the one or more regions of interest selected for removal by the user from regions of interest 312.

In another embodiment, neuroimage mapping manager 300 makes a determination as to whether indicators correlate with the patient's clinical data. Clinical data 336 is data describing the results of clinical laboratory tests. Clinical data 336 may include, without limitation, urinalysis tests, blood tests, thyroid tests, biopsy results, cultures, electrolyte tests, genetic tests, bone marrow tests, tests for the presence of viral agents/illness, tests for the presence of bacterial agents/illnesses, hormone tests, or any other type of laboratory tests. Clinical data 336 describes the presence of substances in the blood, urine, tissue, hormone levels, body chemistry, and body fluids. Clinical data 334 may be relevant to diagnosis or therapy for a particular condition.

Moreover, clinical data 336 may reveal causes of one or more features in the brain scans. For example, clinical tests may indicate mercury poisoning or other substances in the blood that may be responsible for the abnormal appearance of a region in a brain scan. Clinical data 336 for a particular patient may be available on data storage device 306, obtained from a remote data storage device via a network connection, and/or may be manually input to neuroimage mapping manager through input/output device 334. If the features in a region of interest correlate with clinical data 336, neuroimage mapping manager 300 identifies the correlations in result 332. The correlations may be provided as links to information embedded within regions of interest 312 or provided separately from regions of interest 312.

Medical history 338 is a record of the patient's past and current medical treatments, prescribed drugs, medical procedures, diagnoses, treating physicians, known allergies, and/or any other medical information associated with the patient. Neuroimage mapping manager 300 may correlate information in medical history that may be responsible for an appearance or presence of a feature in a region of interest with that particular region in regions of interest 312.

For example, if medical history 338 indicates that the patient suffered a head trauma in a car accident when the patient was a child that led to structural damage in a particular area of the brain, that information is linked to the region of interest corresponding to the area of the brain where the head trauma occurred. Likewise, if the patient had brain surgery to prevent or lessen the effects of seizures and the epilepsy surgery effects brain function in one or more areas of the brain, the regions of interest that are correlated to the areas of the brain effected by the epilepsy surgery are identified in regions of interest 312 with a link to the portion of the patient's medical history 338 discussing the epilepsy surgery and effects of the epilepsy surgery.

Digital video analysis 339 is a software component for generating metadata that describes the behavior of a patient. Digital video analysis 339 receives video data 340 from a set of cameras. The cameras may be any type of camera for capturing video images and/or audio. For example, and without limitation, the camera may be a digital video camera, a still image camera for capturing still images, a moving video recorder for capturing a stream of video images, or any other type of camera. The camera may be stationary or mobile. The set of cameras 602 may be coupled to and/or in communication with computer 301 associated with digital video analysis 339 to transmit video data 340 to digital video analysis 339 via a wired or wireless connection.

Video data 340 includes video images and/or audio data. The video images include images of the patient. The audio data includes sounds made by the patient, such as human speech, crying, whistling, singing, or any other vocalizations. The audio data may also include sounds associated with the patient, such as, without limitation, footfalls, tapping, clapping, running, chewing, drinking, swallowing, blinking, coughing, sneezing, or any other sounds associated with the patient. Video data 340 may be gathered by the set of cameras at anytime.

In one embodiment, video data 340 may be generated while a patient waits to see a medical practitioner, during a medical consultation, during administration of a therapy, during an observations period, while the patient is at home, while the patient is outside a medical facility, such as in a parking lot of a medical complex, or at any other time. For example, the patient may consent to have a set of cameras placed inside the patient's home, in proximity to the patient's home, or in the patient's workplace so that video data 340 may be gathered while the patient is asleep, working, interacting with coworkers, or performing other activities.

Digital video analysis 339 analyzes video data 340 using a set of analytics engines to generate behavioral data 324. Behavioral data 324 is metadata describing the appearance of the patient, the actions of the patient, events associated with the patient, and any other behavior related data. For example, and without limitation, behavioral data 324 may indicate that the patient is wearing multiple layers of clothing on a warm summer day. The behavioral data may describe behavioral tics, such as verbal tics, unprovoked use of profanity, locking and unlocking doors, turning lights on and off, lacing and unlacing shoes, or other repetitive behaviors.

Behavioral data 324 may also describe behaviors, such as, without limitation, pacing, a running monologue or talking with oneself, an appearance of confusion, or other actions. The behavioral data may also describe an appearance of a person's face and emotions apparent on the patient's face. For example, and without limitation, the behavioral data may describe an angry look, such as frowning and dilated pupils in conjunction with utilization of a loud voice and throwing objects to identify angry or hostile behavior. The behavioral data may indicate that the patient sat in a single location, did not speak, did not react to other people or external stimuli, and had a fixed stare for a given period of time to indicate that the patient is unemotional, dissociated, or catatonic.

Cognitive data 342 is data describing results of cognitive tests and psychological evaluations. Cognitive data 342 may include results of Rorschach ink blot tests, memory tests, intelligence quotient (IQ) tests, problem solving, language skills tests, perception tests, and other results of cognitive and psychological evaluations. Cognitive data 342 may be entered by a user manually using input/output 334. Cognitive data 342 may also be generated automatically by cognitive test engine 343. Cognitive test engine 343 is software for administering cognitive tests and psychological tests to a patient. Cognitive test engine 343 may use input/output 334 to present a set of cognitive and psychological test questions to the patient. The patient enters answers using input/output 334. The set of questions may be presented in an audio format, a video format, a tactile format, or a combination of audio, video, and/or tactile format. Cognitive test engine 343 analyzes the patient's responses to set of questions and generates cognitive data 342 based on the answers.

Diagnostic engine 344 is implemented as software for analyzing patient data in diagnosis models 346 to generate quantitative information describing diagnostic characteristics associated with the patient. The patient data may include, without limitation, patient set of scans 304, regions of interest 312, clinical data 336, medical history 338, behavioral data 324, cognitive data 342 or any other medical and/or behavioral data. Diagnoses models 346 comprises analytical engines that parse and/or process patient data to form the quantitative information describing diagnostic characteristics. Diagnostic characteristics are indicators of potential neuropsychiatric conditions. An indicator includes, without limitation, a symptom, a behavior, a test result, a feature of a brain scan, or any other indicator of a given condition. Indicators of neuropsychiatric conditions may include, for example, and without limitation, levels of brain metabolism, structural features of the brain, functional aspects of the brain, behavioral tics, levels of chemicals, such as dopamine and neurotransmitters, and other indicators of neuropsychiatric conditions.

Correlation engine 348 compares the set of indicators of potential neuropsychiatric conditions with diagnostic signatures 350. A diagnostic signature is a signature that corresponds to at least one indicator in the set of indicators. Signature identification 352 generates diagnostic signatures 350 by analyzing medical literature 318 and scans 320 of patients with known neuropsychiatric disorders to identify indicators or signatures of each known neuropsychiatric disorder. For example, and without limitation, if a majority of patients diagnosed with schizophrenia have enlarged brain ventricles, signature identification 352 identifies enlarged brain ventricles as a signature of schizophrenia. Signature identification 352 may also attach a weighting to each signature. For example, if a majority of patients diagnosed with schizophrenia have the enlarged brain ventricles but only thirty percent of patients diagnosed with schizophrenia have a decreased level of metabolism in a particular region of the brain, the signature of enlarged brain ventricles may be assigned a higher weighting than a signature for decreased metabolism in the particular region of the brain. Diagnostic engine 344 optionally uses weighting 354 to identify a diagnosis for the patient.

Diagnostic engine 344 identifies diagnostic signatures that correspond to one or more indicators to form matching signatures. Diagnostic engine 344 identifies a potential diagnosis associated with each matching signature to form set of potential diagnoses 356. Set of potential diagnoses 356 may include a single diagnosis of one condition, as well as diagnoses for two or more neuropsychiatric conditions. Set of diagnoses 356 may optionally include additional information used by diagnostic engine 344 to generate each diagnosis. For example, and without limitation, set of potential diagnoses 356 may include an identification of the indicators of neuropsychiatric conditions, an identification of the matching diagnostic signatures 350, the weighting assigned to each matching diagnostic signature, regions of interest 312, portions of medical literature 330, relevant portions of clinical data 336, relevant portions of medical history 338, and any other information relevant to each diagnosis generated by diagnostic engine 344. In another embodiment, set of potential diagnoses 356 includes a link to the additional information. For example, and without limitation, set of diagnoses 356 may include a link to portions of medical literature 330, a link to regions of interest 312, a link to relevant portions of clinical data 336, a link to relevant portions of medical history 338, a link to matching diagnostic signatures 350 and the weighting for each matching diagnostic signature, as well as links to any other relevant data used to generate each diagnosis.

A potential diagnosis in set of potential diagnoses 356 is a diagnosis of a condition that corresponds to indicators of a particular condition. Set of potential diagnoses 356 may include a percentage of correspondence between the patient's symptoms, clinical data, medical history, and behavior with the signs and symptoms associated with a diagnosis in set of potential diagnosis.

In this embodiment, neuroimage mapping manager 300 and diagnostic engine 334 are located on computer 301. In another embodiment, diagnostic engine 334 may be located on a computing device that is remote from computer 301, such as, without limitation, a remote server. In such a case, diagnostic engine 334 may receive result 332 via a network connection to a network, such as network 102 in FIG. 1. The network may be a intranet, Ethernet, the Internet, a local area network (LAN), a wide area network (WAN), a wireless network, a private network, or any other type of network.

Figure 4:
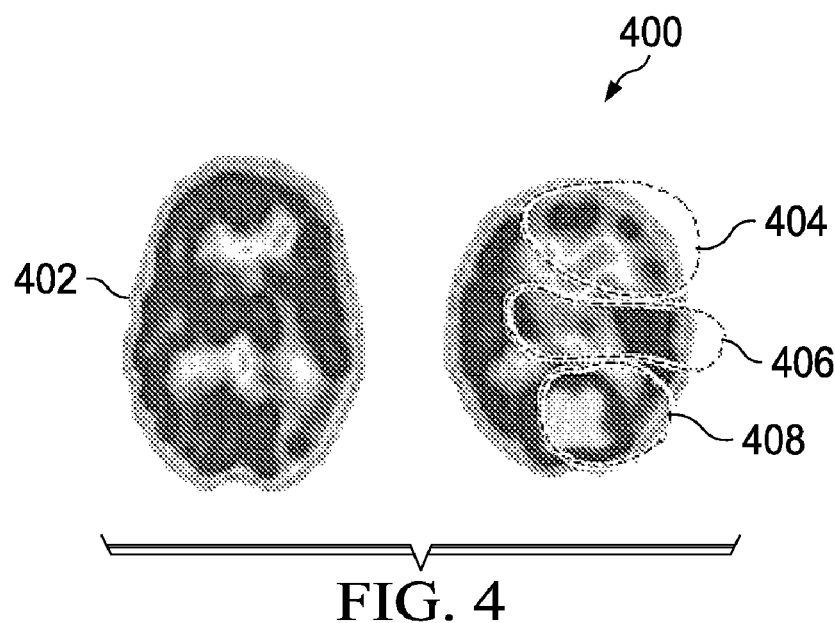
FIG. 4 is a block diagram of a magnetic resonance imaging brain scan having regions of interest in accordance with an illustrative embodiment.

Referring to FIG. 4, a block diagram of a magnetic resonance imaging brain scan having regions of interest is depicted in accordance with an illustrative embodiment. Scan 400 is a positron emission tomography scan of a brain of a patient. Scan 402 is a positron emission tomography scan of a normal, healthy subject. Scan 400 has regions of interest 404-408. Regions of interest 404-408 are areas in scan 400 that show indications of a potential condition, abnormality, chemical imbalance, illness, disease, or other deviation from an expected appearance of the scan. In this example, regions of interest 404-408 show disruptions in brain activity. Region 406 shows abnormal changes in the size of the ventricles of the brain. Region 408 shows decreased function in the frontal section.

Figure 5:
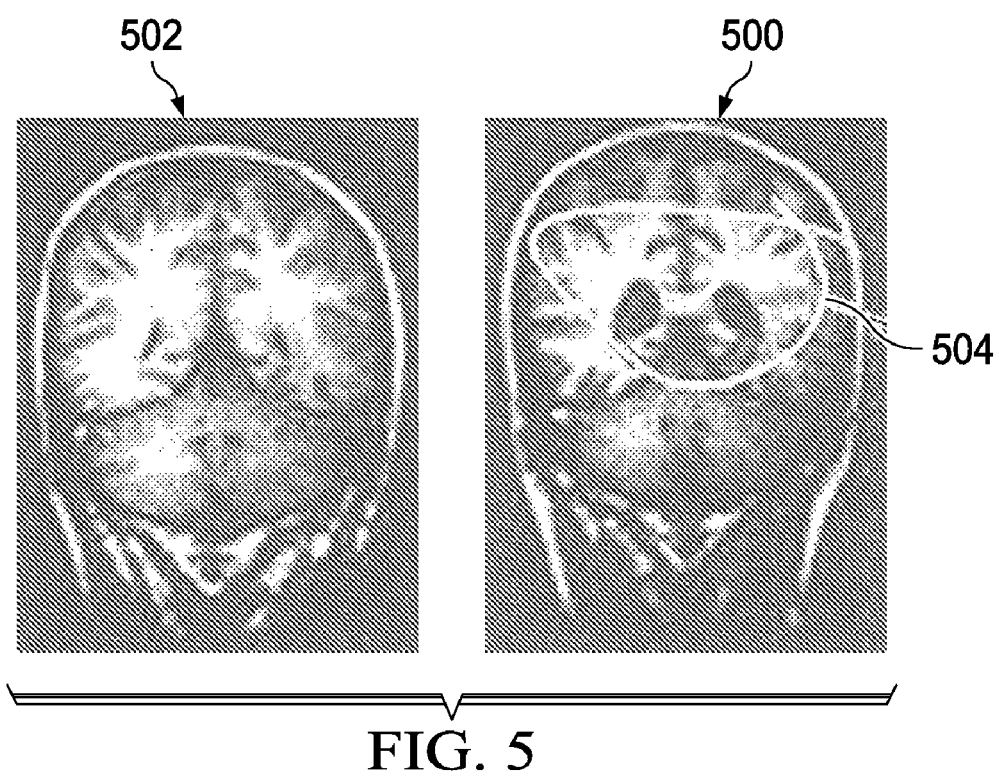
FIG. 5 is a positron emissions tomography brain scan having regions of interest in accordance with an illustrative embodiment.

Turning now to FIG. 5, a positron emissions tomography brain scan having regions of interest is shown in accordance with an illustrative embodiment. Scan 500 is a magnetic resonance imaging scan of a patient's brain. Scan 502 is a magnetic resonance imaging scan of a normal, healthy subject's brain. Scan 500 includes region of interest 504. Region 504 shows an enlargement of the ventricles of the brain when compared with scan 502 of a normal, healthy subject. The enlargement of the ventricles shown in region of interest 504 may indicate an illness or disease, such as, without limitation, schizophrenia. Therefore, a neuroimage mapping manager identifies region 504 as a region of interest.

Figure 6:
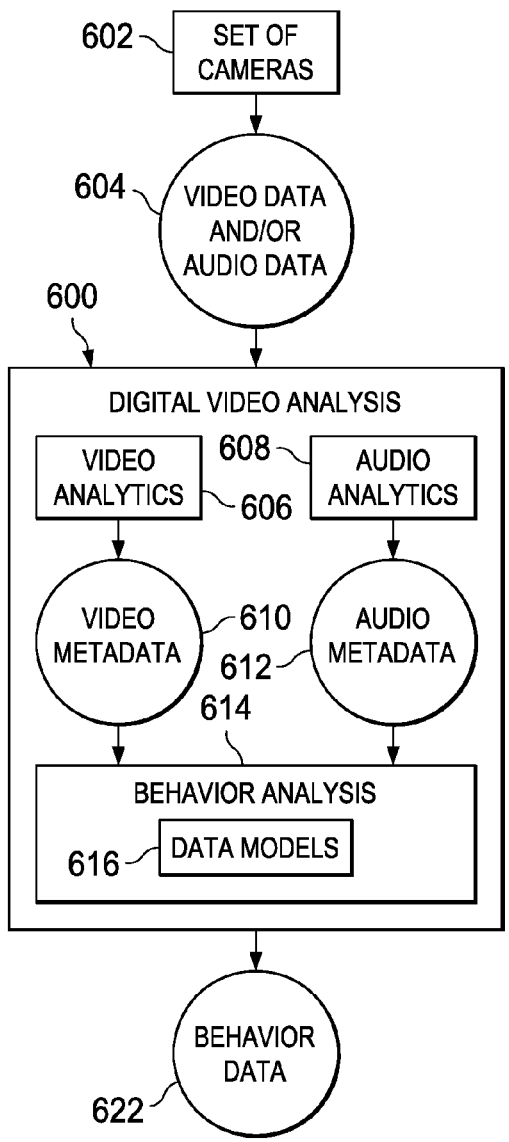
FIG. 6 is a block diagram of digital video analysis for generating behavioral data in accordance with an illustrative embodiment.

FIG. 6 is a block diagram of digital video analysis for generating behavioral data in accordance with an illustrative embodiment. Digital video analysis 600 is software for generating metadata describing the behavior of a patient, such as, without limitation, International Business Machines (IBM) Smart Surveillance System (S3). Set of cameras 602 is a set of one or more cameras. Set of cameras 602 generates video data and/or audio data 604.

Each camera in set of cameras is an image capture device that may be implemented as any type of known or available camera, including, but not limited to, a video camera for taking moving video images, a digital camera capable of taking still pictures and/or a continuous video stream, a stereo camera, a web camera, and/or any other imaging device capable of capturing a view of whatever appears within the camera's range. Various lenses, filters, and other optical devices such as zoom lenses, wide angle lenses, mirrors, prisms and the like may also be used with set of cameras 602. Each camera may be fixed in a particular orientation and configuration or programmable in orientation, light sensitivity level, focus or other parameters. Programming data may be provided via a computing device, such as server 104 in FIG. 1. Each camera may be capable of moving and/or rotating along one or more directions, such as up, down, left, right, and/or rotate about an axis of rotation to follow or track a person, animal, or object in motion. Each camera may be stationary or non-stationary, for example and without limitation, a camera may be coupled to a wall, associated with an employee, a mounted on a mobile robot, mounted on a cart or gurney, or mounted on one or more doors or doorways.

Digital video analysis 600 receives video data and/or audio data 604 from set of cameras 602. Video analysis 606 is a video analytics engine that automatically analyzes video images and generates video metadata 610 describing events occurring in the video data. For example, if the video data is a continuous video stream having images of patient pacing in a circle, video metadata 610 describes the speed at which the patient is pacing, the path along which the patient walks as the patient paces, and any other movements made by the patient as the patient paces.

Audio analytics 608 is an analytics engine that analyzes audio data recorded by a set of microphones and generates audio metadata 612 describing the sounds in the audio data. For example, and without limitation, audio metadata 612 may identify words spoken by the patient, the decibel level of sound, the origination point of the sound, the pitch of the sound, the type of sound, or any other description of the sound. The type of sound is an identification of what made a sound. A type of sound may be a human voice, a human cry, a sound of a footfall, tapping, humming, or any other type of sound. Behavior analysis 614 analyzes video metadata 610 and audio metadata 612 using data models 616 to identify events. The identified events are described in behavioral data 622.

Figure 7:
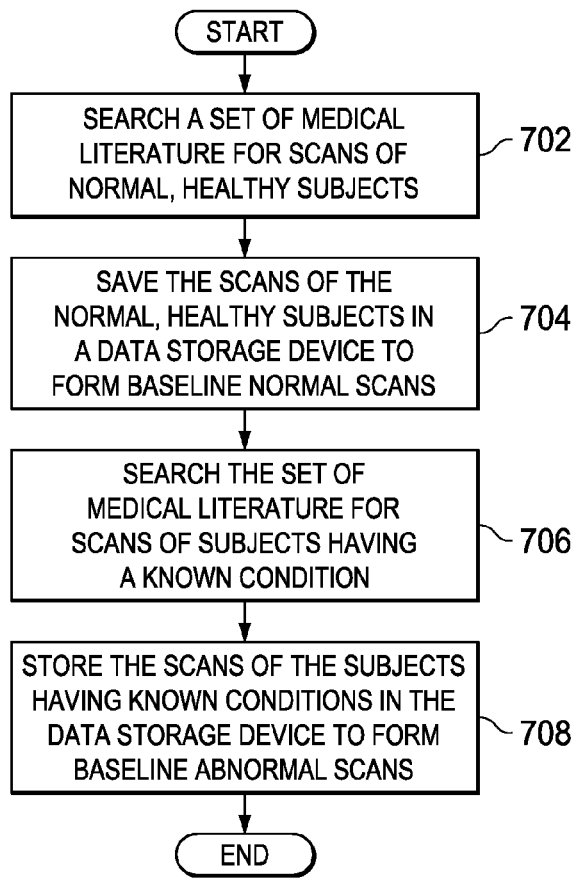
FIG. 7 is a flowchart of a process for generating baseline control scans in accordance with an illustrative embodiment.

FIG. 7 is a flowchart of a process for generating baseline control scans in accordance with an illustrative embodiment. The process in FIG. 7 may be implemented by software for generating a set of baseline control scans, such as medical data and text analytics 314 in FIGS. 3 A and B. The baseline control scans may include baseline normal scans and/or baseline abnormal scans. Baseline normal scans are scans depicting regions of a brain that does not show indications of at least one neuropsychiatric disorder. Baseline abnormal scans are scans depicting regions of a brain that does show one or more indications of at least one neuropsychiatric disorder.

The process begins by searching a set of medical literature sources for scans of normal, healthy subjects (step 702). The scans of the normal, healthy subjects are saved in a data storage device to form baseline normal scans (step 704). The process searches the set of medical literature sources for scans of subjects having known conditions (step 706). The conditions may be a disease, an illness, an infection, a deformity, or any other condition. The scans of the subjects having the known conditions are saved in the data storage device to form baseline abnormal scans (step 708) with the process terminating thereafter.

Figure 8:
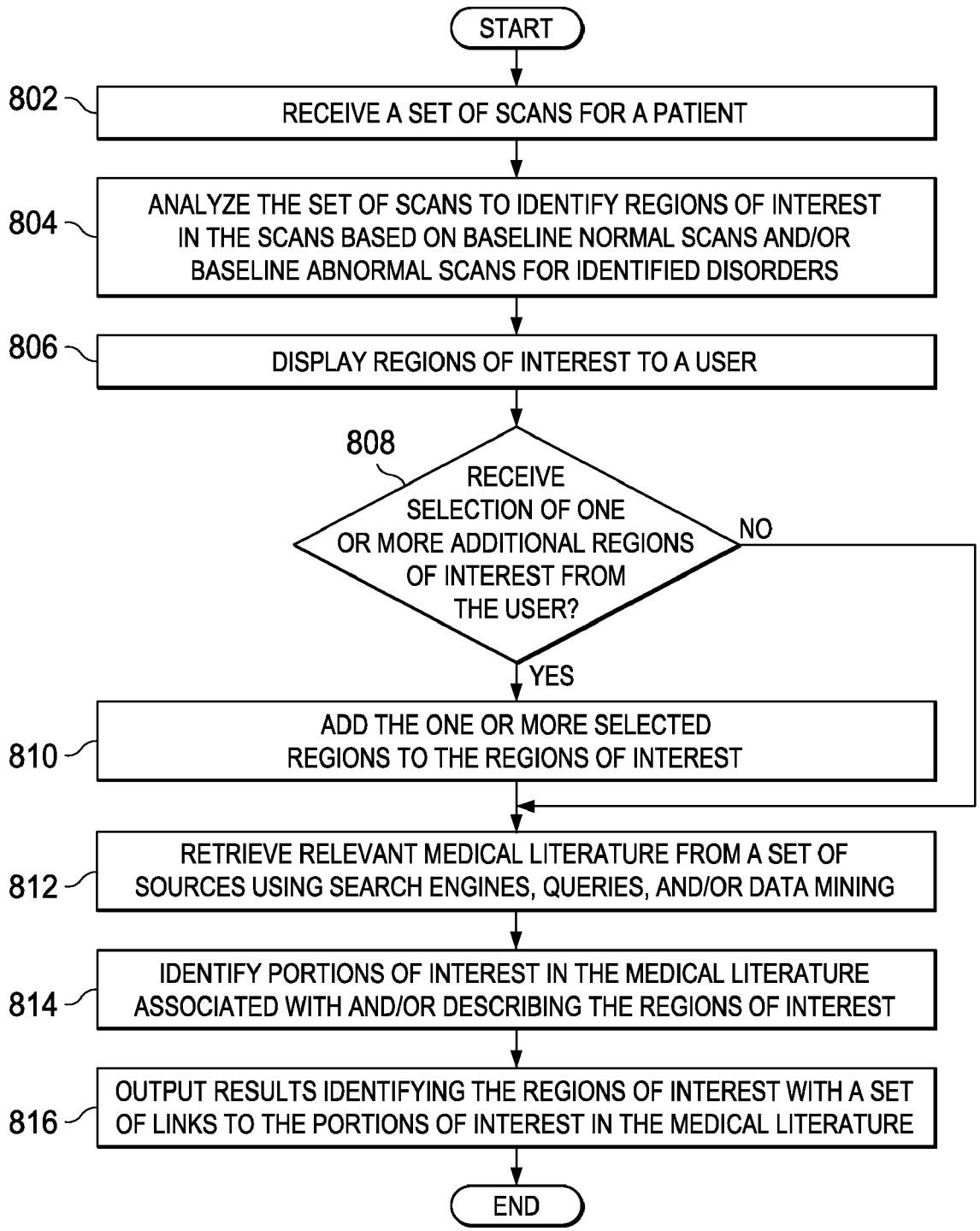
FIG. 8 is a flowchart of a process for identifying regions of interest correlated with relevant portions of the medical interest in accordance with an illustrative embodiment.

FIG. 8 is a flowchart of a process for identifying regions of interest correlated with relevant portions of the medical interest in accordance with an illustrative embodiment. The process in FIG. 8 may be implemented by software for analyzing patient brain scans to identify regions of interest in the brain scans and generate links to portions of interest in the medical literature, such as neuroimage mapping manager 300 in FIGS. 3 A and B.

The neuroimage mapping manager receives a set of scans for a patient (step 802). The set of scans may include functional magnetic resonance imaging (fMRI) scans, structural magnetic resonance imaging (sMRI) scans, positron emission tomography (PET) scans, or any other type of brain scans. The neuroimage mapping manager analyzes the set of scans to identify regions of interest in the scans based on baseline normal scans and/or baseline abnormal scans for identified disorders (step 804). The neuroimage mapping manager displays the identified regions of interest to a user (step 806). The neuroimage mapping manager makes a determination as to whether a selection of one or more additional regions of interest is received from the user (step 808).

If a selection of one or more additional regions of interest is received from the user, the neuroimage mapping manager adds the one or more selected regions to the regions of interest (step 810). After adding the selected regions to the regions of interest at step 810 or if no selections of additional regions are received from the user at step 808, the neuroimage mapping manager retrieves relevant medical literature from a set of sources using search engines, pattern recognition, queries, and/or data mining (step 812). The embodiments are not limited to using only search engines, queries, and data mining. Any known or available method for locating desired information in an electronic data source may be utilized.

Next, the neuroimage mapping manager identifies portions of interest in the medical literature associated with and/or describing the regions of interest (step 814). The portions of interest may include pages, paragraphs, or portions of text describing one or more of the regions of interest, the appearance of one or more of the regions of interest, or the characteristics of one or more of the regions of interest. The portions of interest in the relevant medical literature may include images of scans containing one or more of the regions of interest, portions of text in the medical literature describing diseases, deficiencies, illnesses, and/or abnormalities that may cause the appearance of one or more of the regions of interest or one or more characteristics of the regions of interest, or any other portion of medical literature that is relevant to one or more of the regions of interest in the patient's scans. The neuroimage mapping manager outputs results identifying the regions of interest with a set of links to the portions of interest in the medical literature (step 816) with the process terminating thereafter.

In this embodiment, the regions of interest are displayed to the user and the user is given an opportunity to select one or more additional regions of interest to add to the regions of interest identified by the neuroimage mapping manager. In another embodiment, the regions of interest are not presented to the user prior to identifying the portions of interest in the medical literature. In this embodiment, the user is not required to review the regions of interest and provide input as to whether to add one or more additional regions of interest. In this case, the process may occur completely automatically without any user input during the process of analyzing the patient's scans to identify regions of interest and linking portions of the relevant medical literature to the regions of interest.

Figure 9:
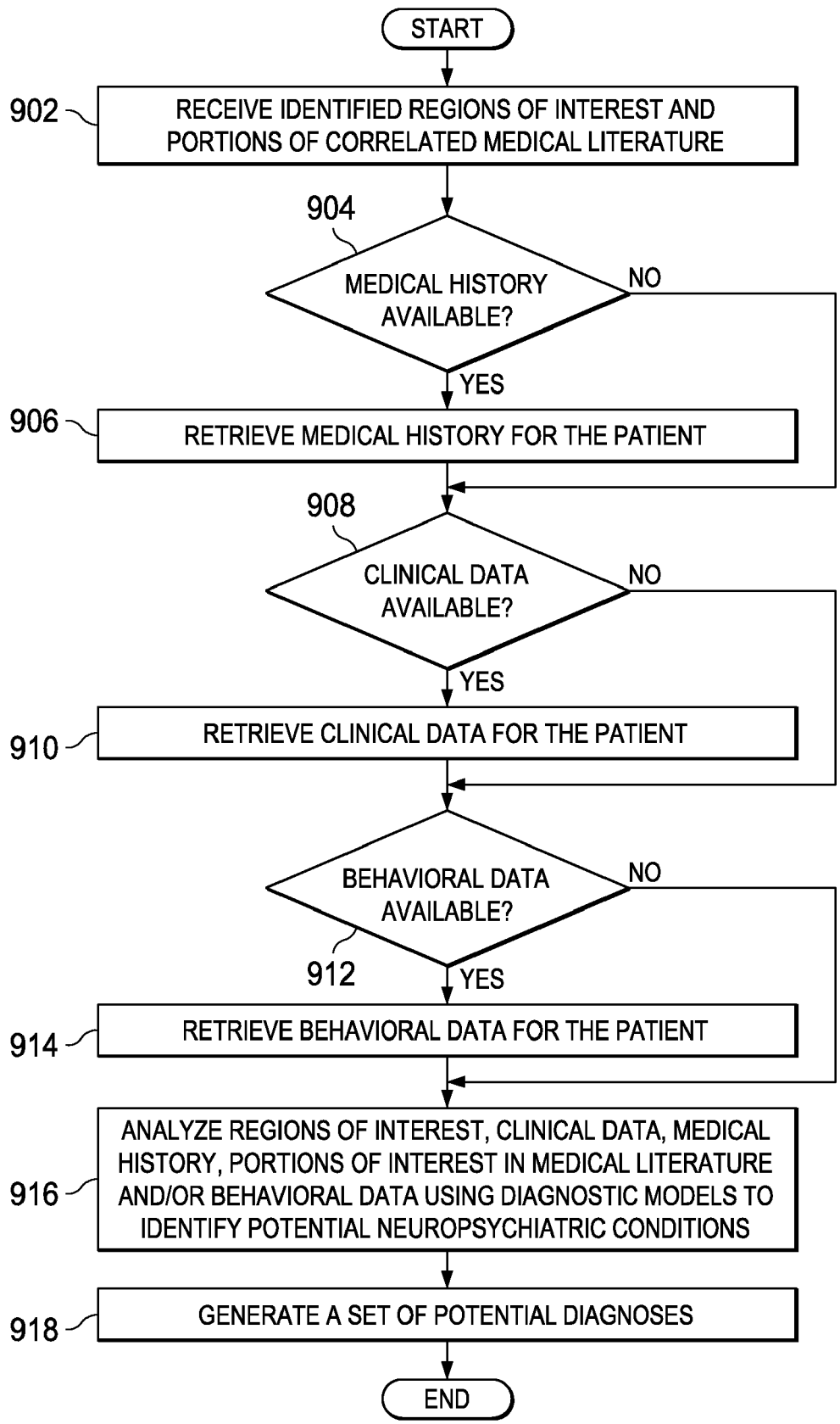
FIG. 9 is a flowchart of a process for generating potential diagnoses for a patient based on quantitative information derived from a set of brain scans in accordance with an illustrative embodiment.

FIG. 9 is a flowchart of a process for generating potential diagnoses for a patient based on quantitative information derived from a set of brain scans in accordance with an illustrative embodiment. The process in FIG. 9 is implemented by software for automatically generating diagnoses based on quantitative data for a patient, such as, without limitation, diagnostic engine 344 in FIGS. 3 A and B.

The process begins by receiving identified regions of interest and correlated portions of medical literature (step 902). A determination is made as to whether a medical history for the patient is available (step 904). If a medical history is available, the medical history is retrieved (step 906). After retrieving the medical history at step 906, or if the medical history is not available at step 906, a determination is made as to whether clinical data is available (step 908). If clinical data is available, the clinical data is retrieved (step 910). After retrieving the clinical data at step 910 or if clinical data is not available at step 908, a determination is made as to whether behavioral data is available (step 912). If behavioral data is available, the behavioral data is retrieved (step 914). After retrieving the behavioral data at step 914 or if behavioral data is not available, the diagnostic engine analyzes the regions of interest, clinical data, medical history, portions of medical literature, and/or behavioral data using diagnostic models to identify potential neuropsychiatric conditions (step 916). The diagnostic engine then generates a set of potential diagnoses (step 918) with the process terminating thereafter.

The steps shown in the flowcharts may be executed in a different order than the order shown in the FIG. 9. For example, clinical data may be retrieved prior to retrieving the medical history or simultaneously with retrieving the medical history. Likewise, the behavioral data may be retrieved prior to retrieving either clinical data or medical history data. Likewise, some of the steps in FIG. 9 may be optional. For example, and without limitation, the process does not require retrieval of clinical data, retrieval of medical history data, or retrieval of behavioral data. Thus, the diagnostic engine may generate a set of potential diagnoses in step 918 without requiring an analysis of clinical data, medical history, and/or behavioral data.

Figure 10:
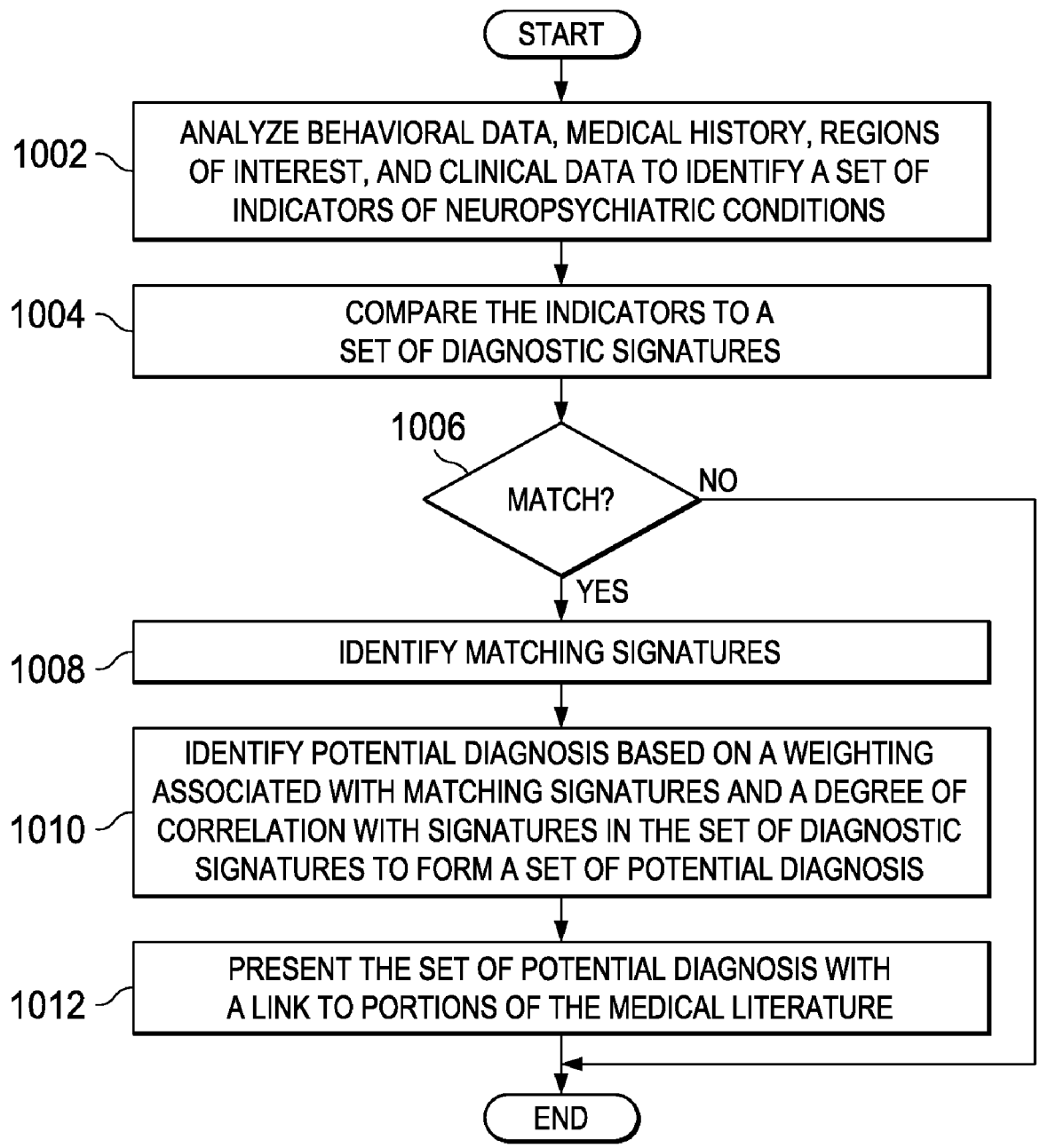
FIG. 10 is a flowchart of a process for automatically generating diagnoses based on diagnostic signatures in accordance with an illustrative embodiment.

FIG. 10 is a flowchart of a process for automatically generating diagnoses based on diagnostic signatures in accordance with an illustrative embodiment. The process in FIG. 9 is implemented by software for automatically generating diagnoses based on quantitative data for a patient, such as, without limitation, diagnostic engine 344 in FIGS. 3 A and B.

The process begins by analyzing behavioral data, medical history, regions of interest, and clinical data to identify indicators of neuropsychiatric conditions (step 1002). The diagnostic engine is not required to have behavioral data, medical history, regions of interest, and clinical data available. The diagnostic engine can identify the indicators using only the regions of interest and portions of the medical literature, the regions of interest, the clinical data, medical history, and behavioral data, or any other combination of these types of information. The diagnostic engine compares the indicators of neuropsychiatric conditions to a set of diagnostic signatures (step 1004). The diagnostic engine makes a determination as to whether any of the diagnostic signatures matches one or more indicators (step 1006). The diagnostic engine identifies the matching signatures (step 1008). The diagnostic engine identifies a potential diagnosis based on a weighting associated with the matching signatures and a degree of correlation between the diagnostic signatures and the one or more indicators (step 1010). The diagnostic engine presents the set of potential diagnoses with a link to one or more relevant portions of the medical literature (step 1012) with the process terminating thereafter.

According to one embodiment of the present invention, a computer implemented method, apparatus, and computer program product for generating neuropsychiatric diagnoses is provided. Quantitative information describing diagnostic characteristics associated with a patient is generated based on an analysis of a set of patient scans. Diagnostic characteristics of interest comprise a set of indicators of potential neuropsychiatric conditions. The quantitative information comprises information associated with regions of interest in the set of scans for the patient. The set of indicators of potential neuropsychiatric conditions is compared with a set of diagnostic signatures. A diagnostic signature comprises a set of indicators of a known neuropsychiatric condition. Matching signatures are identified. A matching signature is a diagnostic signature that corresponds to at least one indicator in the set of indicators to form a set of signatures. A diagnosis associated with each signature in the set of signatures is identified to form a set of potential diagnoses. The set of potential diagnoses is presented. The set of potential diagnosis comprises a link to a portion of the medical literature associated with each diagnosis.

The diagnostic engine automatically identifies indicators of neuropsychiatric disorders based on an analysis of brain scans and the medical literature. The diagnostic engine then automatically generates diagnoses of neuropsychiatric disorders based on the identified indicators. In this manner, the embodiments provide for improved diagnosis of neuropsychiatric disorders without requiring input or intervention by a human user. The diagnostic engine lessens the workload on physicians and researchers, permits more accurate data interpretation and analysis of scans, and allows physicians and researchers to more quickly reach a diagnosis of neuropsychiatric disease. In addition, the diagnostic engine provides a decision support tool for clinicians in both clinical and research settings, to help them identify neuropsychiatric conditions in complex cases, as well as to determine whether a therapy, such as talk therapy, pharmacotherapy, or mechanical electroconvulsive therapy, is effective as depicted via association of neuroimage data with the relevant medical literature. Moreover, the diagnostic engine maps relevant portions of the medical literature onto a patient's scans for diagnosis and identifies indicators of neuropsychiatric conditions for consideration by medical practitioners.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention can take the form of an entirely hardware embodiment, an entirely software embodiment or an embodiment containing both hardware and software elements. In a preferred embodiment, the invention is implemented in software, which includes but is not limited to firmware, resident software, microcode, etc.

Furthermore, the invention can take the form of a computer program product accessible from a computer-usable or computer-readable medium providing program code for use by or in connection with a computer or any instruction execution system. For the purposes of this description, a computer-usable or computer readable medium can be any tangible apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated.

What is claimed is:

1. A computer implemented method executing on a processor for generating neuropsychiatric diagnoses, the computer implemented method comprising:

automatically determining a set of regions of interest in a set of patient scans stored on computer readable storage media based on comparing the set of patient scans with a set of baseline scans stored on computer readable storage media;

generating quantitative information describing diagnostic characteristics associated with a patient based on an analysis of the set of patient scans, wherein the quantitative information comprises a set of indicators of potential neuropsychiatric conditions, the set of indicators including one or more indicators associated with each region in the set of regions of interest in the set of scans for the patient including a first indicator associated with a first region of interest in the set of regions of interest and a second indicator associated with a second region of interest in the set of regions of interest, wherein the first indicator is of a different form than the second indicator;

comparing each of the set of indicators of potential neuropsychiatric conditions with a set of diagnostic signatures, wherein a diagnostic signature comprises a set of indicators describing diagnostic characteristics of a known neuropsychiatric condition;

identifying a plurality of matching signatures, wherein a matching signature is a diagnostic signature describing a first diagnostic characteristic that corresponds to a second diagnostic characteristic described by at least one indicator in the set of indicators to form a set of signatures; and identifying a plurality of diagnoses including a diagnosis associated with each signature in the set of signatures to form a set of potential diagnoses.

2. The computer implemented method of claim 1 further a identifying a weighting associated with each matching signature, wherein a matching signature having a greater weighting is identified as a diagnosis having a higher degree of certainty than a diagnosis associated with a matching signature having a lower weighting.

3. The computer implemented method of claim 1 wherein generating the quantitative information comprises:

deriving the quantitative information from a correlation of the regions of interest with portions of interest in the medical literature.

4. The computer implemented method of claim 1 wherein generating the quantitative information comprises:
    analyzing a medical history for the patient with the regions of interest and portions of interest in the medical literature to form the quantitative information, wherein the medical history comprises information describing previously diagnosed medical conditions of the patient, previously prescribed medications, and currently prescribed medications.

5. The computer implemented method of claim 1 wherein generating the quantitative information comprises:
    analyzing clinical data with the regions of interest and portions of interest in the medical literature to form the quantitative information.

6. The computer implemented method of claim 5 wherein clinical data comprises results of laboratory tests, wherein laboratory tests comprises urinalysis, blood tests, thyroid tests, biopsies, cultures, electrolyte tests, genetic tests, and hormone tests.

7. The computer implemented method of claim 1 wherein generating the quantitative information comprises:
    receiving digital video data from a set of cameras, wherein the digital video data comprises images of the patient;
    analyzing the digital video data in a digital video analysis to form behavioral data, wherein the behavioral data comprises metadata describing actions taken by the patient and events associated with the patient; and
    analyzing the behavioral data with the regions of interest and portions of interest in the medical literature to form the quantitative information.

8. The computer implemented method of claim 1 wherein the set of potential diagnoses further comprises an identification of each indicator in the set of potential neuropsychiatric indicators associated with each diagnosis in the set of diagnoses.

9. The computer implemented method of claim 1 further comprising:
    analyzing cognitive data with the regions of interest and portions of interest in the medical literature to form the quantitative information.

10. The computer implemented method of claim 1 wherein identifying the matching signatures further comprises:
    processing the set of indicators of potential neuropsychiatric conditions in a diagnostic model, wherein the diagnostic model analyzes combinations of indicators in the set of indicators of potential neuropsychiatric conditions and compares the combinations of indicators with each signature in the set of diagnostic signatures to identify the matching signatures.

11. The computer implemented method of claim 1 further comprising:
    presenting the set of potential diagnoses, wherein the set of potential diagnosis comprises a hyperlink to a location on a network where a portion of the medical literature associated with each diagnosis resides.

12. A computer program product for generating neuropsychiatric diagnoses, the computer program product comprising:
    a computer usable medium having computer usable program code embodied therewith, the computer usable program code comprising:
    computer usable program code configured to generate quantitative information describing diagnostic characteristics associated with a patient based on an analysis of a set of patient scans, wherein the quantitative information comprises a set of indicators of potential neuropsychiatric conditions associated with regions of interest in the set of scans for the patient, the set of indicators including a first indicator associated with a first region of interest in the set of regions of interest and a second indicator associated with a second region of interest in the set of regions of interest, wherein the first indicator is of a different form than the second indicator;
    computer usable program code configured to compare the set of indicators of potential neuropsychiatric conditions with a set of diagnostic signatures, wherein a diagnostic signature comprises a set of indicators of a known neuropsychiatric condition;
    computer usable program code configured to identify matching signatures, wherein a matching signature is a diagnostic signature that corresponds to at least one indicator in the set of indicators to form a set of signatures; and
    computer usable program code configured to identify a diagnosis associated with each signature in the set of signatures to form a set of potential diagnoses;
    computer usable program code configured to present a view of each region within the regions of interest;
    computer usable program code configured to automatically search for and identify at least a portion of an electronic medical literature relevant to an indicator associated with each region within the regions of interest;
    computer usable program code configured to present hyperlinks embedded within each view of each region within the regions of interest linking to locations on a network where the at least a portion of the electronic medical literature relevant to the indicator associated for each region within the regions of interest resides; and
    computer usable code configured to present a view of the at least a portion of the electronic medical literature associated with a hyperlink embedded within a view of a region within the region of interest upon receiving from a user a selection of the hyperlink embedded within the view of the region within the region of interest.

13. The computer program product of claim 12 further comprising:
    computer usable program code configured to identify a weighting associated with each matching signature, wherein a matching signature having a greater weighting is identified as a diagnosis having a higher degree of certainty than a diagnosis associated with a matching signature having a lower weighting.

14. The computer program product of claim 12 wherein generating the quantitative information comprises:
    computer usable program code configured to analyze cognitive data with the regions of interest and the portions of interest in the electronic medical literature to form the quantitative information.

15. The computer program product of claim 12 wherein generating the quantitative information comprises:
    computer usable program code configured to analyze medical history for the patient with the regions of interest and the portions of interest in the electronic medical literature to form the quantitative information, wherein the medical history comprises information describing previously diagnosed medical conditions of the patient, previously prescribed medications, and currently prescribed medications.

16. The computer program product of claim 12 wherein generating the quantitative information comprises:

computer usable program code configured to analyze clinical data with the regions of interest and the portions of interest in the electronic medical literature to form the quantitative information.

17. The computer program product of claim 12 wherein generating the quantitative information comprises:

computer usable program code configured to receive digital video data from a set of cameras, wherein the digital video data comprises images of the patient;

computer usable program code configured to analyze the digital video data in a digital video analysis to form behavioral data, wherein the behavioral data comprises metadata describing actions taken by the patient and events associated with the patient; and computer usable program code configured to analyze the behavioral data with the regions of interest and the portions of interest in the electronic medical literature to form the quantitative information.

18. An apparatus comprising:

a bus system;

a communications system coupled to the bus system;

a memory connected to the bus system, wherein the memory includes computer usable program code; and a processing unit coupled to the bus system, wherein the processing unit executes the computer usable program code to generate quantitative information describing diagnostic characteristics associated with a patient based on an analysis of a set of patient scans, wherein the quantitative information comprises a set of indicators of potential neuropsychiatric conditions associated with regions of interest in the set of scans for the patient, the set of indicators including a first indicator associated with a first region of interest in the set of regions of interest and a second indicator associated with a second region of interest in the set of regions of interest, wherein the first indicator is of a different form than the second indicator;

compare the set of indicators of potential neuropsychiatric conditions with a set of diagnostic signatures, wherein a diagnostic signature comprises a set of indicators of a known neuropsychiatric condition;

identify a plurality of matching signatures, wherein a matching signature is a diagnostic signature that corresponds to at least one indicator in the set of indicators to form a set of signatures; and identify a diagnosis associated with each signature in the set of signatures to form a set of potential diagnoses diagnosing a plurality of conditions for the patient, the set of potential diagnoses including a first diagnosis that corresponds with a first portion of the regions of interest and a second diagnosis that corresponds to a second portion of the regions of interest.

19. The apparatus of claim 18 wherein the processor unit further executes the computer usable program code to analyze cognitive data with the regions of interest and portions of interest in medical literature to form the quantitative information.

20. The apparatus of claim 18 wherein the processor unit further executes the computer usable program code to analyze clinical data with the regions of interest and the portions of interest in medical literature to form the quantitative information.

21. A system for generating neuropsychiatric diagnoses comprising:

a processor executing a diagnostic engine, wherein the diagnostic engine automatically generates a set of potential diagnoses based on a set of indicators of neuropsychiatric conditions associated with the patient, wherein the diagnostic engine automatically determines a set of regions of interest in a set of patient scans stored on computer readable storage media based on comparing the set of patient scans with a set of baseline scans, wherein the diagnostic engine accepts user input indicating a first one or more regions of interest not within the set of regions of interest to include in the set of regions of interest, wherein the diagnostic engine accepts user input indicating a second one or more regions of interest within the set of regions of interest to exclude from the set of regions of interest, wherein the diagnostic engine forms a modified set of regions of interest by adding the first one or more regions of interest to the set of regions of interest and by excluding the second one or more regions of interest from the set of regions of interest, wherein the diagnostic engine comprises:

a diagnostic model, wherein the diagnostic model generates quantitative information based on an analysis of the modified set of regions of interest in the set of patient scans, wherein the quantitative information comprises the set of indicators of potential neuropsychiatric conditions, the set of indicators including a first indicator associated with a third region of interest in the modified set of regions of interest and a second indicator associated with a fourth region of interest in the modified set of regions of interest, wherein the first indicator is of a different form than the second indicator;

a correlation engine, wherein the correlation engine compares the set of indicators of potential neuropsychiatric conditions with a set of diagnostic signatures and identifies matching signatures, wherein a diagnostic signature comprises a set of indicators associated with identification of a neuropsychiatric condition, and wherein a matching signature is a diagnostic signature that corresponds to at least one indicator in the set of indicators to form a set of signatures; and wherein the diagnostic engine identifies a diagnosis associated with each signature in the set of signatures to form the set of potential diagnoses.

22. The system of claim 21 further comprising:

a signature identification, wherein the signature identification analyzes a plurality of scans from a set of electronic medical literature sources to generate the diagnostic signatures, wherein the signature identification associates a weighting with each diagnostic signature, and wherein the diagnostic engine generates the set of potential diagnoses based on the matching signatures and a weighting associated with each matching signature.

23. The system of claim 21 further comprising:

a medical data and text analytics component, wherein the medical data and text analytics component searches a set of electronic medical literature sources for medical literature relevant to the modified set of regions of interest to form relevant portions of medical literature, wherein the set of electronic medical literature sources comprises medical literature in an electronic form, and wherein the diagnostic engine analyzes information in the relevant portions of the medical literature with the modified regions of interest to identify the set of indicators.

24. The system of claim 21 wherein the diagnostic engine analyzes any available clinical data, medical history information for the patient, cognitive data, and portions of medical literature associated with the modified regions of interest, with the matching signatures to generate the set of potential diagnoses.

25. The system of claim 24 further comprising:
a cognitive test engine, wherein the cognitive test engine automatically presents a set of cognitive and psychological test questions to the patient; and analyzes patient responses to the set of cognitive and psychological test questions to form the cognitive data.

* * * * *